(12) United States Patent
Wells et al.

(10) Patent No.: US 6,613,367 B1
(45) Date of Patent: Sep. 2, 2003

(54) INFANT FORMULA

(75) Inventors: John Cowper Kingston Wells, Gloucestershire (GB); Robert Johan Joseph Hageman, Wageningen (NL); Günther Boehm, Echzell (DE); Gilda Georgi, Friedrichsdorf (DE); Günther Sawatzki, Münzenberg (DE); Jacob Geert Bindels, Zoetermeer (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/889,691

(22) PCT Filed: Jan. 20, 2000

(86) PCT No.: PCT/NL00/00043

§ 371 (c)(1), (2), (4) Date: Oct. 24, 2001

(87) PCT Pub. No.: WO00/42868

PCT Pub. Date: Jul. 27, 2000

(30) Foreign Application Priority Data

Jan. 20, 1999 (EP) .............................................. 99200166
Apr. 29, 1999 (EP) .............................................. 99201359

(51) Int. Cl.[7] .......................... A23L 1/302; A23L 1/305; A23C 9/20
(52) U.S. Cl. .......................... 426/72; 426/590; 426/656; 426/801
(58) Field of Search .......................... 426/72, 590, 656, 426/801

(56) References Cited

U.S. PATENT DOCUMENTS 3,415,655 A * 12/1968 Hino et al.

FOREIGN PATENT DOCUMENTS

| DE | 41 30 284 | 3/1993 |
|---|---|---|
| EP | 0 007 691 | 2/1980 |
| EP | 0 482 715 | 4/1992 |
| EP | 0 891 719 | 1/1999 |
| WO | WO 87/01590 | 3/1987 |
| WO | WO 91/10441 | 7/1991 |

OTHER PUBLICATIONS

Hidehiko Yokogoshi et al., "Meal Composition and Plasma Amino Acid Ratios: Effect of Various Proteins or Carbohydrates, and of Various Protein Concentrations," *Metabolism*, V. 35, 1986, pp. 837–842.

* cited by examiner

*Primary Examiner*—Helen Pratt
(74) *Attorney, Agent, or Firm*—Young & Thompson

(57) ABSTRACT

The invention relates to products for complete nutrition of infants. The products are characterized by the type and amount of protein and carbohydrate and the increased levels of folic acid, vitamin B6 and vitamin B12 or their functional equivalents. These products improve feelings of well-being of infants, especially those of young age, and are useful in the treatment and prevention of diseases that are associated with disorders of serotonin- and melatonin metabolism.

12 Claims, No Drawings

INFANT FORMULA

FIELD OF THE INVENTION

The invention is related to infant formulae, i.e. artificial products for complete nutrition of infants, for improving feelings of well-being, compensation of immaturity and problems in the metabolic capacity of the infant. The nutritional products provide complete nutrition to the infant and their composition is characterised by a selected protein and carbohydrate composition and the increased amounts of folic acid, and vitamin B6 and B12 or their functional analogues.

BACKGROUND OF THE INVENTION

At present a large part of the population of babies in industrialised countries are fed with specialised infant formulae. It has been reported that consumption of these formulae is associated with several medical problems that may occur at young age, such as increased frequency of gastrointestinal problems and decreased immune status, but perhaps also at later age, because infants that are exclusively fed with human breast milk would score better on these parameters. It has also been reported that infants that are exclusively fed with these artificial formulae suffer from longer episodes of crying compared to those that are fed with human breast milk. This suggests a general feeling of discomfort due to perhaps hunger, pain or even medical problems. These problems may delay development of the child and produce concerns and practical problems to the parents.

In a first aspect of the invention it is aimed to develop a new infant formula for complete nutrition that decreases the number of crying episodes and promotes sleeping behaviour for the child, especially for infants of young gestational age.

In a second aspect it is also aimed to develop infant formulae that compensate for the relatively small capacity of the (rapidly developing) metabolic systems of the child shortly after birth. This leads to improved health, formation of higher quality new tissue (visual acuity, intellectual capacities, etc.), a better immune status and a decrease in occurrence of periods of increased bilirubin plasma levels (hyperbilirubinaemia or jaundice). Increased bilirubin levels are known to occur relatively often within the first 3 weeks after birth. Some of the negative effects of this disorder have been described in the prior art, including the inhibition by bilirubin of the uptake of the neurotransmitters dopamine and glutamate by the synaptic vesicles and the neurotoxic effects that this disease state may have.

Conventional infant formulae have been developed that mimic the composition of human breast milk to a degree that can be achieved at a reasonable price. These formulae are normally based on cow's milk proteins like casein or mixtures of casein and whey. In case of problems, such as metabolic disorders or allergic reactions, other protein sources are used like hydrolysates or soybean proteins; alternatively the allergic component is replaced by another non-allergenic ingredient. However, the composition of these formulae still differs from that of human breast milk. The relatively low levels of tryptophan and cysteine/cystine can be compensated for by increasing the amount of protein in the product. However, this increases the amount of threonine to very high levels and increases the costs of the formulae. Also the imbalances with regard to the ratio of tryptophan to the sum of the large neutral amino acids will be maintained.

In a third aspect of the invention, it is therefore aimed to develop a formula that provides amounts of tryptophan, cysteine and threonine that are more similar to the levels provided by human breast milk as an exclusive source, while at the same time the ratio of the amounts of tryptophan to large neutral amino acids in the product is more similar to the ratio observed in human breast milk. Plasma levels of the amino acids in infants that are exclusively fed with the new composition will therefore be more similar to those observed in infants that are exclusively fed with human breast milk. At the same time the costs and taste of the nutritional product will be acceptable.

Serotonin (5-hydroxytryptamine) is an important neurotransmitter, especially in the central nervous system. It also behaves as a strong contractor of smooth muscles, for example those in the arterioles and bronchioles, when released from mast cells and platelets. Serotonin is claimed to be involved in the release of peptic hormones in the gastrointestinal tract. Abnormalities in serotonin metabolism have been linked to several disorders of the central nervous system such as those related to pain, sleep and mood, either by direct action of serotonin or via its role as precursor for melatonin. Serotonin is synthesised from tryptophan by hydroxylation and subsequent decarboxylation. Tryptophan has to pass the blood brain barrier first, before it can be converted in the brain to serotonin. This passage occurs via a receptor that also transfers the large neutral amino acids.

"Large neutral amino acids" are understood to be valine, isoleucine, leucine, tyrosine and phenylalanine. In order to obtain relatively large amounts of tryptophan in the brain, competition by these amino acids has to be low and consequently the ratio of plasma concentrations of tryptophan and the sum of the large neutral amino acids has to be large.

It has been found that threonine also uses this same receptor. It is now recognised that, because of the relatively large amounts of threonine in conventional cow's milk sweet whey, the corresponding high threonine plasma levels significantly hinder the passage of tryptophan over the blood brain barrier. In a fourth aspect of the invention it is therefore aimed to provide an infant formula that ensures an increased ratio of the plasma concentrations of tryptophan to the sum of the large neutral amino acids plus threonine.

After consumption of carbohydrates, insulin is released from the pancreas. This latter component is known to reverse the catabolic processes in the body, that may have resulted from a period of starvation prior to the (re)feeding of the child, into anabolic processes. As long as sufficient glucose is present in the plasma, plasma insulin levels remain sufficiently high to prevent catabolism of (in particular muscle) tissue and the resulting release of branched chain amino acids (BCAA, valine, isoleucine and leucine). In a fifth aspect, the invention is therefore aimed at developing an infant formula that provides an insulin response on a short term, with a sufficient longer-term effect as well.

It is now recognised that the insulin response must also last until about the next feeding of the infant. Young infants are fed every 2–8 hours. It is equally important that infants maintain appetite and will eat every time a sufficient amount of food in a short time, to ensure sufficient growth. In a sixth aspect of the invention, it is therefore aimed to develop a formula that, after consumption, satisfies the infants during a period of at least 1–6 hours and preferably for a period up to 3 hours, and restores appetite of the infant after 3 hours.

Infants, especially those of young gestational age, are extremely sensitive to consumption of excess amounts of food components and imbalances in the consumption pattern of these components, predominantly due to their low relatively metabolic—and clearance capacity. This is caused by inherited problems and immaturity of their enzymatic systems and the small capacity of their organs. Infants are also sensitive to imbalances in neurotransmitter levels in the brain. It is therefore dangerous to transfer concepts that are developed for adults to infant formulae. The composition of human breast milk is therefore mostly taken as "golden standard". In a seventh aspect of the invention a nutritional product is aimed at that does not cause any toxic reactions in normal use and to deviate as little from the golden standard as is justified.

It is important to recognise that all the aspects as mentioned above must be achieved at the same time, in order to improve well-being satisfactorily without causing negative effects to the child.

The biochemical roles of folic acid, vitamin B6 and B12 are described in the art. To the best of the knowledge of the inventors, it is nowhere described or indicated that consumption of the combination of these vitamins, in amounts as given in the claims, is crucial for increasing well-being and normalising behaviour, senses of pain, and mood of the infant. It was found that the restrictions in protein and carbohydrates composition, that are present for infant formulae, necessitate the increase in these vitamins in order to have an optimal effect. It is also not earlier disclosed that inclusion of these vitamins in the amounts as claimed, significantly enlarges the group of infants that benefit from such infant formulae, especially with regard to increase of well-being, the improvement of other serotonin- or melatonin-mediated disorders.

In Table 1, the composition of a typical formula for infants younger than 4 months is compared with that of human breast milk and that of a formula according to the invention. For the purpose of comparing these formulae with compositions as described in the prior art, it is useful to relate the composition to the amount of components that will be consumed per kg body weight per day.

TABLE 1

[0016]: Comparison of the composition of Nutrilon Premium, human breast milk and a composition according to the invention.

| Component | IMF* | HBM** | Invention |
|---|---|---|---|
| Energy (kcal/100 ml) | 67–70 | 65–68 | 63–71 |
| Crude Protein (g/100 ml) | 1.2–1.8 | 0.7–0.8 # | 0.7–1.5 # |
| Arg (% = g/100 g protein) | 3.0–3.5 | 4.9 | 3.4–5.0 |
| Trp (%) | 1.3–1.5 | 3.0 | 1.6–3.5 |
| BCAA (g/100 g protein) | 22–25 | 25.5 | 19–25 |
| Tyr + Phe | 7–9 | 12.4 | 7–11 |
| Thr | 5–7 | 6.0 | 3–6 |
| Cys | 1.0–1.6 | 1.9 | 1.5–3.6 |
| Carbohydrates = CHO (g/100 ml) | 4–7.5 | 7 | 5.7–10.5 |
| Lactose (% = g/100 g CHO) | 80–100 | 99 | 0–100 |
| Maltodextrins (%) | 0–20 | 0 | 0–100 |
| Folic acid ($\mu$g/100 kcal) | 15 | 4–21 | 30–200 |
| Vitamin B6 ($\mu$g/100 kcal) | 60 | 10–46 | 50–130 |
| Vitamin B12 ($\mu$g/100 kcal) | 0.3 | 0.02–1 | 0.1–20 |
| Zinc (mg/100 kcal) | 0.6 | 0.2–0.8 | 0.4–1 |
| Vitamin B2 ($\mu$g/100 kcal) | 150 | 40–90 | 80–300 |
| Niacin (mg niacin equivalents/100 kcal) | | | 0.55–2.0 |

Notes:
*As an example of a typical IMF (= infant milk formula) was taken a formulae based on 40–60% whey and 40–60% casein
**Average values for mature human breast milk
these protein levels are specified as real protein which is defined to be the amount of protein + amino acids and peptides.

Conventional infant formulae provide about 63–71 kcal/100 ml. This value is recommended in order to provide 100–130 kcal/kgbw.d, which is generally assumed to be mandatory for adequate growth by the child. Typical protein levels in commercially available infant formulae are 1.2–1.8 g/100 ml. This leads to a consumption of 2.0–2.4 g protein per kgbw.d. Typical tryptophan levels in the proteins as used in the manufacturing of infant formulae are 1.3–1.5%. This results in typical intakes of 26–36 mg tryptophan per kgbw.d by infants. In conventional infant formulae, in which the protein composition is formed by mixing 60% sweet whey and 40% casein, the ratio of the amounts of tryptophan to the total amount of large neutral amino acids (Phe, Tyr, Val, Ile, Leu) is about 4.4–4.7/100. When threonine is considered as a large neutral amino acid, the ratio becomes 3.7–3.9/100. These values become smaller when more casein is used in the product.

Table 1 does not provide data for all food components. Some components are less important for the invention and are therefore not explicitly; specified. However, the product according to the invention requires inclusion of these components in amounts as present in conventional infant formula, except in those situations as indicated in the text.

Conventional infant formulae do not support optimally well-being of the child, because the tryptophan levels are much too low, especially compared to the sum of the amounts of large neutral amino acids plus threonine. Also, the amounts of all three essential vitamins, being folic acid, vitamin B6 and B12 are insufficient to support bio-synthesis and metabolism, including the serotonin metabolism, in the young child.

WO 87/01590 (=EP-A-238533, Kreitzman) discloses a slimming diet for adults that provides per day less than 1000 kcal (so less than 14 kcal/kgbw.d; less than 700 kcal/day is preferred), less than 100 g protein (which results in <1.4 g protein/k gbw per day for a 70 kg person; always more than 30 g and less than 46 g protein is preferred) and more than 0.5 g tryptophan (more than 3 g is preferred). The product is unsuitable for feeding infants due to too high protein levels and potential toxicity of the amount of tryptophan that is included. The product should also not be used for combating obesity of the infant.

EP-A-007691 (Wurtman) discloses a formula for suppression of appetite for carbohydrates in adults, that comprises tryptophan, in an amount of 10–100 mg/kgbw.d, and carbohydrates, but no branched-chain amino acids. The ratio of the amounts of tryptophan and carbohydrates in the formula must be 1:3–50. The product is unsuitable for use in infants, because infants require branched chain amino acids at young age for growth. In addition the amount of carbohydrates should always be more than 25 times the tryptophan level in a formula.

Medgennix, in WO 91/10441 (=EP-A-463154), discloses compositions that comprise polypeptides containing more than 2.2% tryptophan as well as arginine or ornithine for providing a "serotinergic effect". The product is developed for combating obesity in adults and treating feelings of depression. No reference is made to infant formulae. Preferably α-lactalbumin is used as a source of tryptophan, which possesses a high ratio of tryptophan to large neutral amino acids plus methionine. Vegetable proteins are suggested as attractive ingredients, because of their relatively high amount of arginine and relatively low levels of phenylalanine and tyrosine. The latter two amino acids are however essential amino acids and recommended daily intakes should be ensured.

Laboratoire Oenobial discloses in WO 98/14204 the use of α-lactalbumin as nutritional complement or medicine for regulating sleep, especially when a jet lag is observed. Consumption of 100 mg and 250 mg α-lactalbumin is claimed to be effective in adults. No relation is made to use in infants nor is indicated that vitamins might play a role in regulating sleep. Alpha-lactalbumin was shown to have a value of the ratio of tryptophan to the sum of the large neutral amino acids is about 0.074 and that of the ratio Cys to Trp equals about 1.47, while the amount of tryptophan is relatively high (about 3.0%).

Heine discloses the use of hydrolysed α-lactalbumin as protein source in infant formulae in DE-A4130284. Use of this protein hydrolysate was claimed in order to achieve a clear separation with β-lactoglobulin and thus administer a better balanced composition with regard to threonine, tryptophan and cysteine/cystine. No reference was made to specific positive effects that can be obtained by using intact α-lactalbumin with regard to feelings of well-being nor the support of insufficiently functioning metabolic systems by using the products of the invention. Neither was indicated that folic acid, vitamin B12 and B6 play a crucial role in these respects. The products disclosed by Heine are also more expensive and have a worse taste compared to the products of the present invention.

DETAILED DESCRIPTION OF THE INVENTION

The characteristics of the composition according to the invention are described in the claims and Table 1 and in more detail below.

Energy density: The energy density of the product is similar to that of prior art products and is in the range of 62–73 kcal/100 ml liquid or reconstituted product. Preferably the energy density is in the range of 64–71 kcal/ml.

Proteins: Protein levels in a product can be determined with the classical Kjeldahl method. The result reflects the crude proteins that are present. For the purpose of this invention we define the protein level as the amount of real proteins plus the amount of amino acids, their salts and peptides; so non-protein nitrogen is excluded. In the products of the invention the protein levels will be in the range of 1.0–3.0 g per 100 kcal, especially between 1.0 and 2.4 g/100 kcal, which allows complete satisfaction of the infants protein needs. An amount of 1.5–2.2 g/100 kcal is most preferred. The higher protein levels, such as from 2.0 or from 2.4 to 3.0 are especially suitable in combination with increased levels of folic acid, vitamin B6 and/or vitamin B 12. Conventional proteins like those from cow's milk or soybeans can be used as basic protein sources, as they provide sufficient amounts of all essential amino acids but also branched-chain amino acids.

In order to increase the amount of L-tryptophan in the product, free L-tryptophan, or a functional equivalent thereof like tryptophan salts or tryptophan-rich peptides, can be suppleted. If free L-tryptophan is used, special care is taken to remove all impurities that might cause toxic reactions. It is further preferred to use a tryptophan source that is stable under the conditions that the infant formula is manufactured. A suitable source is a tryptophan-rich protein or a hydrolysate or extract thereof. If proteins are used as ingredient, it is obvious that the levels of the large neutral amino acids and threonine are relatively low. However they should not be that low, that the recommended daily intakes are not met. Examples of suitable proteins in this respect are acid whey, α-lactalbumin, egg protein and proteins from meat and wheat, and mixtures of two or more of these components. Acid whey protein or unhydrolysed α-lactalbumin are especially preferred, because of the excellent amino acid profile and the sustained release pattern in young children compared to hydrolysates thereof or compared to a combination of mixtures of alternative dairy products and suppleted sources of tryptophan, cysteine or arginine. Tryptophan should be present in the product in an amount of 1.6–3.5 g, especially 1.7–3.5 g per 100 g of the total protein component and preferably in an amount of 1.9–2.8 g/100g protein.

The value of the ratio of the amounts in the product of tryptophan and the sum of the large neutral amino acids must be in the range 4.8–10 and preferably in the range 5.5–8.5/100, and most preferably 6.2–8.2/100.

When threonine is also considered as a large neutral amino acid, the value of the ratio must be in the range 4.1–8.0 and preferably in the range 4.7–7.5.

In order to ensure sufficiently high levels of cysteine, whey proteins or egg proteins can be included in the formula. If whey proteins are used, acid whey is recommended, in order to avoid too high threonine levels.

It is especially preferred to have a relatively high ratio of Cys/Trp in the range of 0.8–1.4, in order to support optimally inclusion of cysteine in liver proteins and in glutathione, which is required for optimal growth and immune function.

In order to increase insulin response arginine or lysine can be supplied as L-forms of the free amino acid or as their functional equivalents. Functional equivalents of amino acids can for example be their salts, synthetic peptides, or proteins that are rich in the particular amino acid, or extracts or hydrolysates of these proteins. Also mixtures of proteins can be included. For example mixtures of 40% casein and 60% whey could be suppleted with the hydrochloric salts of L-tryptophan or L-arginine. It is however preferred to include arginine in a form that is slowly released such as by using a granulate or similar system that comprises an arginine salt like L-arginine.HCl, or by using partially pea protein, or a hydrolysate or extract thereof, in order to extend the insulin effect. The total amount of arginine plus lysine should exceed 200, preferably exceed 250 mg/kg, e.g. 280 mg/kgbw.d. The amount of protein that is required for providing this amount of arginine can be calculated from this number and the concentration of arginine or lysine in this protein.

Carbohydrates: According to the invention, the amount of carbohydrates in the formula must be in the range of 9–15 g/100 kcal (35–60 en %), and preferably in the range of 11–14 g/100 kcal. This results in a carbohydrate content of 5.7–10.5 g per 100 ml of liquid or reconstituted product. The ratio of the amount of carbohydrates to the amount of tryptophan will exceed 20 and preferably 50, and go up to 940, preferably up to 450. The weight ratio of carbohydrates to protein is preferably from 5 to 14, most preferably from 6 to 12.

It is preferred to use, at least partly, maltodextrins, apart from the lactose that may be present in the formula. This will ensure a fast availability of glucose units in plasma and therefore a fast insulin response. However, it is preferred to include at least 50% of the carbohydrates as lactose, except in those cases that the product will be used by lactose-intolerant infants. If maltodextrins are used it is advantageous to use maltodextrins having a degree of hydrolysis of 10–15 dextrin equivalents, in order to decrease the sweetness of the product.

Folic acid: Folic acid can occur in nature in many forms. Typically it is suppleted to infant formulae as monoglutamate. Though according to the invention basically all functional equivalents of folic acid can be used, it is preferred to use the monoglutamate form for obtaining best bioavailability. It is essential to include at least 30 μg, and preferably more than 44 μg per 100 kcal. If higher amounts of folic acid are consumed, a larger group of infants will show an improved serotonin- and melatonin metabolism, even if the amounts of tryptophan are relatively low as in conventional infant formulae. This is especially true if the amount of folic acid is above 50 μg per 100 kcal and sufficient vitamin B12 is made available, as is the case when the formula is suppleted with more than 0.6 μg/100 kcal, as is indicated below.

Vitamin B12: Vitamin B12 is normally present in infant formula partially as a complex with dairy proteins and predominantly as suppleted cyanocobalamine. Before it is absorbed the complex has to be split in the stomach and the released cyanocobalamine has to bind to a factor that is released from the stomach. Once absorbed, cyanocobalamine or alternative forms have to be converted to methylcobalamine, before they can be used as a cofactor that catalyses the conversion of homocysteine to methionine. Both absorption and conversion of cyanocobalamine occur ineffectively in part of the population of young infants.

According to the invention it is therefore required to supplete at least 0.1 μg, and preferably more than 0.8 μg vitamin B12 per 100 kcal, preferably as hydroxycobalamine, in order to support serotonin biosynthesis and metabolism effectively. Instead of vitamin B12, metabolic equivalents, i.e. compounds that lead to endogenous formation of vitamin B12, can also be used.

When indigestible carbohydrates are added to the product or other bifidogenic measures are taken, these are selected in such a way that the biosynthesis capacity of the gut flora is not imparted or even is stimulated.

Vitamin B6: Vitamin B6 is active in the cells as pyridoxal phosphate. However pyridoxine or pyridoxamine are frequently used as source of this vitamin, because of the stability of these compounds. Infants, especially those of young age, have a restricted capacity to convert these compounds to the active form. It has been found that a simple increase in the dose may decrease the intracellular pyridoxal phosphate levels. It is therefore preferred to include in the formula 50–130 μg vitamin B6 per 100 kcal. If higher amounts of vitamin B6 are suppleted it is not recommended to use pyridoxine. Also mixtures of pyridoxamine and pyridoxal can be used.

Zinc: Because zinc is essential for biosynthesis of pyridoxal phosphate, it is mandatory that the amount of zinc is in the range of 0.4–2 mg/100 kcal, preferably from 0.4 to 1.0 mg/100 kcal. Zinc can be included as a zinc salt, such as zinc sulphate or as complex with amino acids or other components.

Niacin equivalents: Niacin functions in the human body as precursor of NAD and can be synthesised from tryptophan in the adult liver. This predominantly occurs when excess tryptophan is present. Biosynthesis of niacin is supported in the young child by the characteristic features of the composition as claimed. This permits the availability of sufficient niacin to support the metabolic processes in the child. These can be further supported by increase of the included amount of niacin to a level of 1.2–5 mg/100 kcal.

Apart from the essential components as indicated above, other microingredients may advantageously be included in a complete infant formula, according to EEC 91/321 or corresponding Regulation: these include: Betaine (preferably at least 5 mg, more preferably at least 30 mg per 100 kcal), choline; taurine (preferably at least 5 mg per 100 kcal), inositol, calcium, phosphorus, magnesium, iron, manganese, copper, iodine, sodium, potassium, chloride selenium, fluoride, carnitine, nucleotides, cholesterol, vitamin A, vit. D, vit. E, vit K, thiamine, riboflavin, pantothenic acid, biotin, and ascorbic acid.

Fats are included in the range of 40–57 en %. The composition of the fat can be selected from prior art compositions. Specially preferred are the ones that are disclosed in any of the earlier patents of patentee, e.g. EP-A-404058, EP-A-231904, EP-A-784437 and DE 19644518, which are incorporated by reference. The essential fatty acids that are present must preferably have the cis-configuration. Alpha-linolenic acid (=ALA): 1.75–4.0% and linoleic acid (LA): 8–35% of total fatty acids; the ratio LA/ALA=5–16.

The product of the invention can have the form of liquid or a powder, that can be reconstituted with water to produce a ready to feed formulation. It can also have the form of a meal that is used for weaning purposes or similar product evident to a person skilled in the art. The liquid products can be packaged in bottles, cartons and the like. The powdered products can be packaged in vacuumised packs, cans or sachets and other suitable forms that are known to a person skilled in the art.

It has been found that daily consumption of the infant formulae as described in the claims results in the benefits as described below:

improves feelings of well being by the infants, supporting regular eating and sleeping patterns helps to compensates for insufficient capacity of the metabolic systems, especially in the young infant consumption of these formulae results in plasma levels of amino acids that are more similar to those of infants, that are exclusively fed with human breast milk, compared to consumption of conventional formulae does not give negative side effects to the infant therefore improves health and immune status and supports growth of high quality has an excellent taste and can be produced at acceptable costs.

EXAMPLE 1

A liquid infant formula having the composition as presented in table 2 was prepared.

TABLE 2

Composition of liquid infant formula
Values are in mg per 100 ml, except where indicated differently.

| | |
|---|---|
| Protein (60% sweet whey, 40% casein) | 1400 |
| Added Trp | 10 |
| Added Arg | 10 |
| Lactose | 7500 |
| Maltodextrins (10–15 DE) | 1600 |
| Fat (EP-231904) | 3100 |
| Na | 18–25 |
| K | 60–100 |
| Cl | 40–60 |
| Ca | 50–85 |
| P | 20–50 |
| Mg | 4.5–6 |
| Fe | 0.5–0.9 |
| Zn | 0.6–1.3 |
| Cu | 40–60 μg |
| Mn | 5–20 μg |

TABLE 2-continued

Composition of liquid infant formula
Values are in mg per 100 ml, except where indicated differently.

| | |
|---|---|
| Se | 1.5–2.2 µg |
| I | 5–15 µg |
| Vitamin A | 80–90 RE |
| β-Carotene | 0–40 µg |
| Vitamin D | 1–1.6 µg |
| Vitamin E | 0.8–1.4 mg TE |
| Vitamin K | 4–20 µg |
| Thiamine | 35–45 µg |
| Riboflavin | 110–150 µg |
| Niacin | 0.7–1.0 mg NE |
| Pantothenate | 0.25–0.35 |
| Biotin | 1.5–1.7 µg |
| Ascorbic acid | 5–10 |
| Taurine | 4–7 |
| Folic acid (added as monoglutamate) | 25–32 µg |
| Vitamin B12 (added as hydroxycobalamine) | 0.4–0.7 µg |
| Vitamin B6 (added as pyridoxine) | 50–65 µg |

EXAMPLE 2

A powdered infant formula having the same composition as in table 2 is prepared. After reconstitution with water it produces a ready-to-feed liquid formula.

EXAMPLE 3

A liquid infant formula having the same composition as in table 2 is prepared, except that:

a) the protein component consists of 50% acid whey, 10% α-lactalbumin and 40% casein, and 5 mg tryptophan/100 ml is suppleted, and b) amounts of microingredients are similar to those of table 2, except folic acid 50 µg/100 ml and cyanocobalamine 1.4 µg/100 ml.

EXAMPLE 4

A liquid formula based on 80% casein and 20% whey having 2.5 crude protein/100 kcal leading to 2.4 g real protein/100 kcal is obtained. Per 100 ml is added 20 mg L-tryptophan and 20 mg N-acetylcysteine. Microingredients are according to table 2.

What is claimed is:

1. A product for complete nutrition of an infant, comprising total protein, being the total of proteins, peptides and amino acids, in the range of 1.0–3.0 g per 100 kcal, the protein being characterised by:
    (a) providing 1.7–3.5 g tryptophan per 100 g total protein, and
    (b) having a weight ratio of tryptophan to the sum of the large neutral amino acids valine, isoleucine, leucine, tyrosine and phenylalanine in the range of 4.8–10:100.

2. A product according to claim 1, in which the total protein is characterised by:
    (a) providing 1.9–2.8 g tryptophan per 100 g protein, and/or
    (b) having a weight ratio of tryptophan to the sum of the large neutral amino acids in the range of 5.5–8.5:100.

3. A product according to claim 1, in which the protein is characterised by a weight ratio of tryptophan to the sum of the large neutral amino acids times plus threonine in the range of 4.1–8.0:100.

4. A product according to claim 1, in which the protein has a weight ratio of cysteine plus cystine to tryptophan in the range of 0.8–1.4.

5. A product according to claim 4, comprising 2.0–3.0 total protein per 100 kcal.

6. A product according to claim 1, the product being characterised by providing per 100 kcal at least one of the following:
    more than 30 µg folic acid,
    more than 50 µg vitamin B6, and/or
    more than 0.1 µg vitamin B12.

7. A product according to claim 1, comprising 9–15 g of carbohydrates per 100 kcal and having a weight ratio of the amount of carbohydrates to tryptophan above 25 up to 940.

8. A product according to claim 1, in which tryptophan and/or cysteine are present in polypeptide form.

9. A product according to claim 8, in which unhydrolysed α-lactalbumin or acid whey is used as polypeptide.

10. A product according to claim 1, characterised by providing per 100 kcal:
    (a) more than 44 µg folic acid, and
    (b) more than 0.8 µg vitamin B12.

11. A product according to claim 1, in which hydroxycobalamin is used as a source of vitamin B12 and pyridoxal or pyridoxamine as a source of vitamin B6.

12. A product according to claim 1, which contains at least 5 mg betaine, and/or at least 5 mg taurine per 100 kcal.

* * * * *